(12) United States Patent
Germanow et al.

(10) Patent No.: US 8,282,280 B2
(45) Date of Patent: Oct. 9, 2012

(54) DISPOSABLE BAG FOR HYGIENIC DISPOSAL OF A FEMININE HYGIENE PRODUCT

(75) Inventors: John W. Germanow, Pittsford, NY (US); Ann D. Germanow, Pittsford, NY (US)

(73) Assignee: Scensible Source Co., LLC, Pittsford, NY (US)

( * ) Notice: Subject to any disclaimer, the term of this patent is extended or adjusted under 35 U.S.C. 154(b) by 1342 days.

(21) Appl. No.: 11/884,226

(22) PCT Filed: Oct. 27, 2006

(86) PCT No.: PCT/US2006/042063
§ 371 (c)(1),
(2), (4) Date: Aug. 9, 2007

(87) PCT Pub. No.: WO2007/050928
PCT Pub. Date: May 3, 2007

(65) Prior Publication Data
US 2008/0212903 A1   Sep. 4, 2008

Related U.S. Application Data

(60) Provisional application No. 60/731,387, filed on Oct. 28, 2005.

(51) Int. Cl.
| | |
|---|---|
| *B65D 33/16* | (2006.01) |
| *B65D 33/10* | (2006.01) |
| *B65D 30/00* | (2006.01) |
| *B65D 33/00* | (2006.01) |
| *B65D 1/34* | (2006.01) |

(52) U.S. Cl. ............ 383/77; 383/8; 383/37; 383/105; 206/554

(58) Field of Classification Search ............ 383/42, 383/77, 120, 8, 71, 37, 105; 604/385.02; 206/554
See application file for complete search history.

(56) References Cited

U.S. PATENT DOCUMENTS

D28,240 S   2/1898   Wellhouse
(Continued)

FOREIGN PATENT DOCUMENTS
CH   528 900   11/1972
(Continued)

OTHER PUBLICATIONS

Machine translation of Japanese Document No. 8-26402 to Nakagawa. Translated on Dec. 28, 2011.*

(Continued)

*Primary Examiner* — Jes F Pascua
(74) *Attorney, Agent, or Firm* — Kenneth J. Lukacher

(57) ABSTRACT

A bag (10) of thin plastic material shaped into a container having a closed end (11*b*) and an open end (11*a*) cut to provide two tying portions (18), and gusseted sides (14) extending between the open and closed ends. The plastic material is of a color and has embedded fragrance and antimicrobial agents, and has an imprinted design or pattern. The bag (10) is of a size suitable for receiving a single product, such as a used feminine hygiene product, along with any other material in the use or replacement of such product by a user, in which the tying portions (18) are tieable to seal said product within the bag. When a product is sealed in the bag (10) by a user, the antimicrobial agents inhibits the growth of odor causing bacteria, the scent masks any odors, and the color and imprinted design assists to conceal or obfuscate any blood on a used feminine product when received within the bag (10).

29 Claims, 6 Drawing Sheets

U.S. PATENT DOCUMENTS

| | | | |
|---|---|---|---|
| 1,808,375 A | | 6/1931 | Plooster |
| 2,478,412 A | * | 8/1949 | McMahan .................... 206/581 |
| 2,750,033 A | * | 6/1956 | Pickens ......................... 206/361 |
| 2,766,927 A | * | 10/1956 | Wallace ........................... 383/89 |
| 3,052,399 A | * | 9/1962 | Brown .......................... 383/204 |
| 3,186,626 A | * | 6/1965 | Shvetz ............................ 383/37 |
| 3,193,181 A | * | 7/1965 | Konjevich et al. .......... 229/87.15 |
| 3,260,170 A | | 7/1966 | Barraclough |
| 3,346,173 A | | 10/1967 | Smith et al. |
| 3,505,432 A | | 4/1970 | Neuwald |
| 3,580,486 A | | 5/1971 | Kugler |
| 3,774,838 A | | 11/1973 | Christie |
| 4,619,361 A | * | 10/1986 | Thomas, Jr. .................. 206/204 |
| 4,742,908 A | * | 5/1988 | Thomas et al. ............... 206/204 |
| 4,753,538 A | | 6/1988 | Jorda |
| D302,112 S | | 7/1989 | Benoit |
| 4,867,339 A | | 9/1989 | Hahn |
| 4,896,773 A | | 1/1990 | Zilio |
| 5,118,022 A | | 6/1992 | Farahnik |
| D342,017 S | | 12/1993 | Boyle |
| D351,100 S | | 10/1994 | Bradley |
| 5,394,834 A | | 3/1995 | Queen et al. |
| 5,509,571 A | | 4/1996 | Weber |
| 5,685,643 A | | 11/1997 | Stary |
| 5,732,716 A | | 3/1998 | Utecht |
| D401,846 S | | 12/1998 | Nguyen |
| 5,884,771 A | * | 3/1999 | McCormick .................. 206/581 |
| 5,890,810 A | | 4/1999 | Barlow |
| 5,950,818 A | | 9/1999 | Paulsen |
| 6,059,100 A | | 5/2000 | Jones |
| 6,095,686 A | | 8/2000 | Mohrmann |
| 6,286,713 B1 | * | 9/2001 | Chan et al. ....................... 221/49 |
| 6,457,863 B1 | | 10/2002 | Vassallo |
| 6,688,466 B2 | | 2/2004 | White et al. |
| 6,702,116 B2 | | 3/2004 | Hummel |
| 6,702,147 B2 | | 3/2004 | Ashford |
| 6,723,080 B1 | | 4/2004 | Habib et al. |
| 6,739,114 B2 | | 5/2004 | Shaffer |
| D494,852 S | | 8/2004 | Meador et al. |
| 6,799,695 B1 | * | 10/2004 | Borrero ........................... 221/59 |
| 7,147,129 B1 | * | 12/2006 | Menefield ...................... 221/283 |
| 7,210,848 B2 | | 5/2007 | Barbier et al. |
| D545,215 S | | 6/2007 | Germanow et al. |
| 7,497,623 B2 | * | 3/2009 | Thomas et al. .................. 383/63 |
| 2002/0133134 A1 | | 9/2002 | Wilbon |
| 2003/0192290 A1 | | 10/2003 | Shaffer |
| 2003/0223657 A1 | * | 12/2003 | Belias et al. .................. 383/105 |
| 2004/0141663 A1 | * | 7/2004 | Gillis et al. ...................... 383/42 |
| 2005/0069227 A1 | * | 3/2005 | Steele ............................... 383/7 |
| 2005/0098466 A1 | * | 5/2005 | Thomas ........................ 206/440 |
| 2005/0145523 A1 | | 7/2005 | Zander et al. |
| 2005/0154365 A1 | * | 7/2005 | Zander et al. ............ 604/385.04 |
| 2006/0030469 A1 | * | 2/2006 | Patridge et al. ............... 493/162 |
| 2006/0045391 A1 | | 3/2006 | Reglar |
| 2007/0055213 A1 | | 3/2007 | Erekson |
| 2007/0116384 A1 | | 5/2007 | Mason |
| 2007/0189643 A1 | | 8/2007 | Tresenfeld |
| 2007/0239127 A1 | * | 10/2007 | Bridges .................... 604/385.13 |
| 2008/0154221 A1 | | 6/2008 | Thornton |

FOREIGN PATENT DOCUMENTS

| | | | |
|---|---|---|---|
| DE | 202 12 283 U1 | | 1/2004 |
| EP | 1 413 272 A1 | | 4/2004 |
| GB | 2 060 398 A | | 5/1981 |
| GB | 2 386 108 A | | 9/2003 |
| GB | 2 392 098 A | | 2/2004 |
| JP | 08026402 A | * | 1/1996 |
| JP | 08033676 A | * | 2/1996 |
| JP | 2003199786 A | * | 7/2003 |
| JP | 2005118205 A | * | 5/2005 |
| WO | WO 94/20378 | | 9/1994 |
| WO | WO 00/15515 | | 3/2000 |
| WO | WO 03/097113 A1 | | 11/2003 |

OTHER PUBLICATIONS

Nappy Sacks and Pop-ins, CeDo Ltd. Web page at http://www.cedo.com/productnappysacks_main.htm, Oct. 25, 2006.

Sanitary Bag Dispenser Refill Pack, Guest International Ltd. Web page at http://www.guestint.co.uk/store/Detail.aspx?pid=125, 2005.

Personal Care, Personal Disposal Bag, Rochester Midland Corp., Web page at http://www.rochestermidland.com/division/perscare/feminine/L_PersonalDisposal.htm, 2000.

Lady Mate Scented Sanitary Disposal Bags, Nisway Corp. Brochure.

Scoop Mate, Scented Petwaste Bags, web page at http://www.scoopbags.net, printed Oct. 25, 2006.

Heaven Scent Hygiene Bags, web page at http://www.alibaba.com/catalog/10905148/Heaven_Scent_Hygiene_Bags.html, printed Oct. 25, 2006 and Heaven Scent Hygiene Bags, web page at http://www.alibaba.com/catalog/100194068/Heaven_Scent_Hygiene_Bags.html, printed Mar. 10, 2008.

Sassy, Diaper Sacks, Web page at http://www.sassybaby.com, printed Oct. 25, 2006.

Ruffles Retail Trash Bags, Covalence Plastics Co. Web page at http://www.covalenceplastics.com/site/content/retail/retail.asp, 2006.

Simply Discrete, Web page at http://www.simplydiscrete.com, printed Nov. 12, 2007.

Simply Discrete, Feminine Protection Disposal Products, Web page at http://www.simplydiscrete.com/6.html?sm=38127, printed Nov. 12, 2007.

Sanitary Disposal Unit, Webside printouts from www.sdunit.com (2004).

Heaven Scent Hygiene Bag, Web site printout from hvsent.com, Mar. 10, 2008.

TESS Printout of U.S. Trademark Reg. 2,865,721 for Heaven Scent Discrete Scented Hygiene Bags.

Guest Supply, guestsupply.com, PVC Sanitary Bags.

* cited by examiner

TIE BAG HANDLES TIGHTLY TO CLOSE. TOSS BAG INTO WASTE RECEPTACLE

PLACE USED PAD, PANTY LINER OR TAMPON IN BAG. DON'T FORGET THE WRAPPER AND APPLICATOR.

GENTLY PULL ONE BAG FROM PACK

DISPOSABLE BAG FOR HYGIENIC DISPOSAL OF A FEMININE HYGIENE PRODUCT

This application claims the benefit of priority to U.S. Provisional Patent Application No. 60/731,387, filed Oct. 28, 2005, which is herein incorporated by reference.

FIELD OF THE INVENTION

The present invention relates to a disposable bag for hygienic disposal of a feminine hygiene product, and relates particularly to an antimicrobial, scented, colored, imprinted bag for storing and then disposing of a used feminine hygiene product. The bag provides clean, easy and discreet disposal of such feminine hygiene product (e.g., pads, tampons, sanitary napkins, and panty liners). The bag may also be used for disposal of other individual products, where hygienic discreet disposal is desired, such as a used adult incontinence product. The present invention also provides a method for hygienic disposal using such bag, and a portable dispenser for the bags.

BACKGROUND OF THE INVENTION

Plastic scented films in the form of long tubes have been used for disposal of diapers in stand-along units, such as the Diaper Genie by Playtex Products of Westport Conn., USA, in which the tube is dispensed from a container in the unit and then drawn and twisted by the user between used diapers to minimize odors there from. When the unit is full, the tube and diapers individually captured therein are disposed of.

Other units have been developed for disposal of sanitary napkins and tampons, such as the Sanitary Disposal Unit manufactured by SDU of Australia, which has a liner bag which is compressed by the user between inserted sanitary napkins and/or tampons. The user is instructed to first wrap the used product in toilet paper or a wrapper prior to insertion in the Sanitary Disposal Unit. When the unit is full, the bag is removed for disposal and replaced with a new bag. Such bags in the Sanitary Disposal Unit are scented and have anti-bacterial characteristics, and are large enough to store in the unit up to 15 sanitary items. Thus, these bags are not practical for separate use outside of a Sanitary Disposal Unit for discreet personal disposal of an individually used feminine hygiene product, as they are too large and bulky for such purpose. Moreover, such units for storing sanitary items are not typically present in public bathrooms, rather often a container with a hinged lid is present for disposing used items, and as a result such container can become unsightly when opened, unsanitary, and can leak odors. Thus, a small discreet bag is desirable for disposal of a used feminine hygiene product that is available from stall mounted dispenser units or easily portable in a purse or handbag, and especially bags which are scented, sealable, and anti-microbial to resist growth of odor causing bacteria. Furthermore, such a small discreet bag when sealed may be disposed in normal trash bins, thus avoiding the expense of providing, cleaning, and maintaining separate disposal containers specially for used feminine hygiene products in public bathrooms, and avoiding clogged plumbing and waste-water pollution when used feminine hygiene products are improperly disposed in toilets.

Scented purple bags are sold by CeDo Ltd. of Telford, Shropshire, UK under the names Pop-ins or Ladymate for disposal of used feminine hygiene products. However, these bags despite tying portions are not anti-microbial, and thus after receiving a used feminine hygiene product can become odorous. Also, these bags can become unsightly, as their colored plastic material is practically see-through and do not sufficiently conceal used feminine hygiene contents. Thus, it would further be desirable to provide a small discreet bag that is in addition to being anti-microbial to resist growth of odor causing bacteria assists in concealing bag contents to the human eye.

SUMMARY OF THE INVENTION

Accordingly, one feature of the present invention is to provide an antimicrobial, scented, colored disposable bag for a used individual feminine hygiene product that can be easily sealed to contain such product therein, which can also be used for individual hygienic disposal of any other used product, such as an adult incontinence product.

Another feature of the present invention is to provide an antimicrobial, scented, colored disposable bag for hygienic disposal of a used product, which has an imprinted design that in addition to bag color assists to conceal or obfuscate from view, any unsightly blood on a used feminine product when received within the bag.

A further feature of the present invention is to provide antimicrobial, scented, imprinted, colored disposable bags that can be located in a dispenser for single bag dispensing therefrom.

A still further feature of the present invention is to provide antimicrobial, scented, imprinted, colored disposable bags that are small and discreet for disposing a used individual hygiene product.

Briefly described, the present invention embodies a bag of thin plastic material having a closed end and an open end cut to provide two ending tying (or handle) portions, and gussets allowing for expansion along the sides of the bag extending between the open and closed ends. The plastic material is of a color (e.g., pink), and has embedded fragrance (or scent) and antimicrobial agent(s). When a product is placed in the bag by a user, the tying portions are knotted to seal the bag close with the product inside, in which the antimicrobial agents inhibits the growth of odor causing bacteria, the scent masks any odors, and the color assists in concealment of contents in the bag.

The bag may be imprinted with a design or pattern. The imprinted design, and the selected bag color (e.g., pink) and the color of the imprint (e.g., darker reddish pink color) assists to conceal or obfuscate blood on a used feminine product when received within the bag. Also, the bag may be of a size limiting such bag to receiving only one used product along with any other used material typically present in the use or replacement of such product by the user. Such material in the case of a feminine hygiene product may be non-human bodily material, for example, a wrapper, or a plastic or cardboard inserter or applicator.

When the bag contains a used feminine product, it need not be wrapped in toilet paper or any wrapper or material prior to being located in bag as the tied bag efficiently seals the used product, eliminating risk of leakage. Further, since the used product is sealed in the bag it may be hygienically placed in a container specifically designed in public bathrooms, or disposed of within a general waste product basket, bin, or receptacle without risk of contact by user or cleaning personnel to the contents' potential infectious diseases, or the risk of cross-contamination.

The present invention also provides a method for hygienic disposal of a used product comprising the steps of: providing a bag of color plastic imprinted material embedded with fragrance and antimicrobial agents, inserting in the bag a used product, tying two portions extending from the bag to retain the product within the bag, and disposing the tied bag in a receptacle capable of receiving a plurality of ones of the bag with a used product.

The product to be received and sealed in the bag of the present invention may be a used feminine hygiene product, or a used adult incontinence product, or any other individual product where hygienic, discreet disposal is desired.

BRIEF DESCRIPTION OF THE DRAWINGS

The foregoing features and advantages of the invention will become more apparent from a reading of the following description in connection with the accompanying drawings in which.

DETAILED DESCRIPTION OF THE INVENTION

Figure 1:
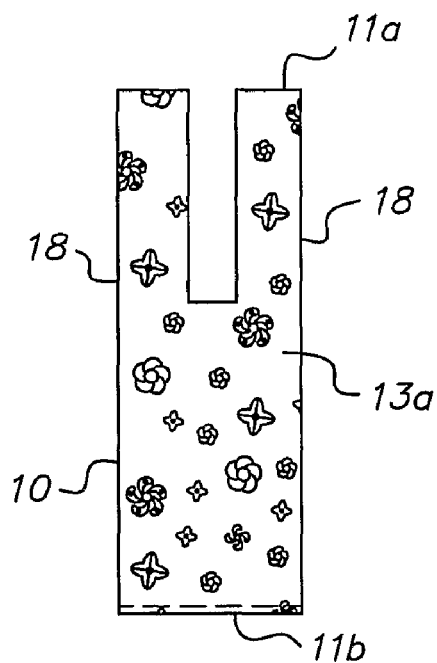
FIGS. 1 and 2 are front and back elevational views, respectively, of a bag in accordance with the present invention in which the bag lies flat with gussets folded inward, such as in a condition prior to use of the bag.
Figure 2:
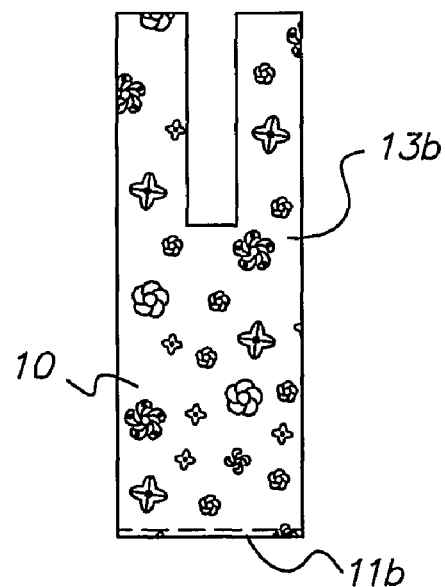
Figure 3:
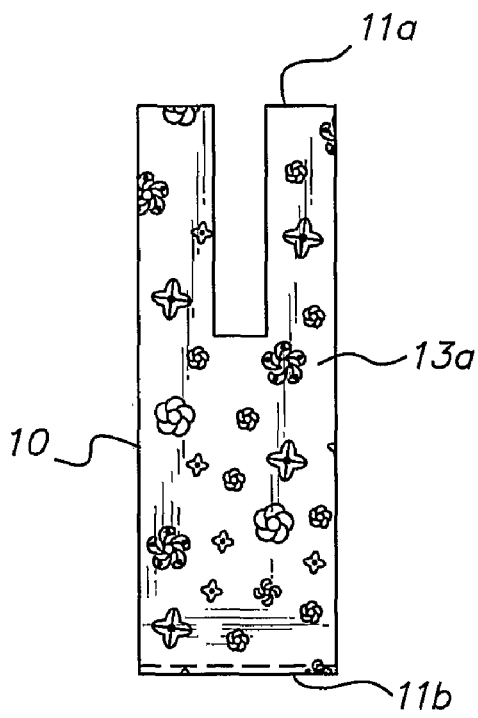
FIGS. 3 and 4 are front elevational views, respectively, of the bag of FIGS. 1 and 2 when the bag is in open condition ready to receive a product.
Figure 4:
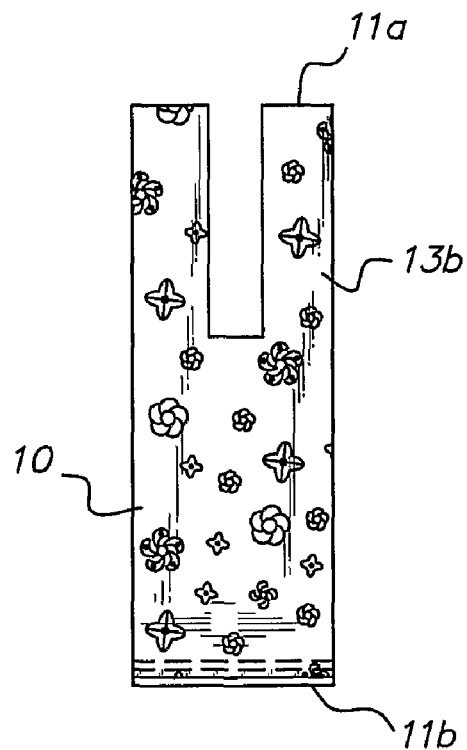
Figure 5:
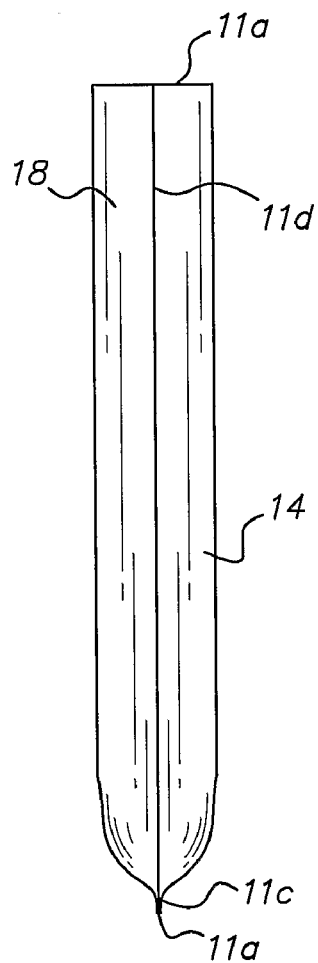
FIGS. 5 and 6 are side elevational views thereof when in said open condition, from the left and right sides, respectively.
Figure 6:
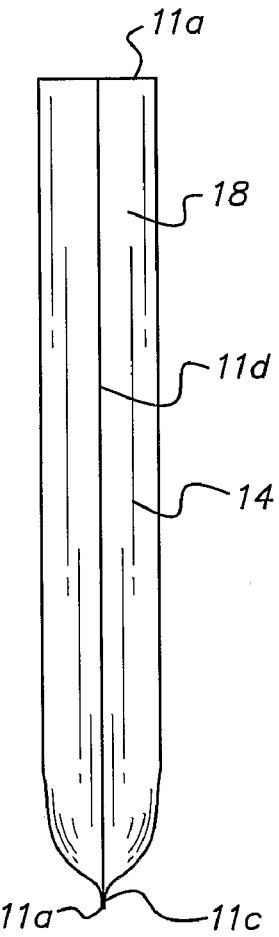
Figure 7:
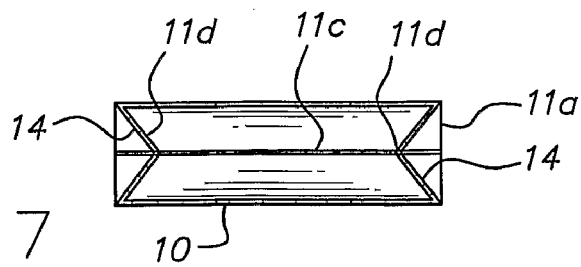
FIGS. 7 and 8 are top and bottom views, respectively, of the bag of FIGS. 3 and 4 in the open condition.
Figure 8:
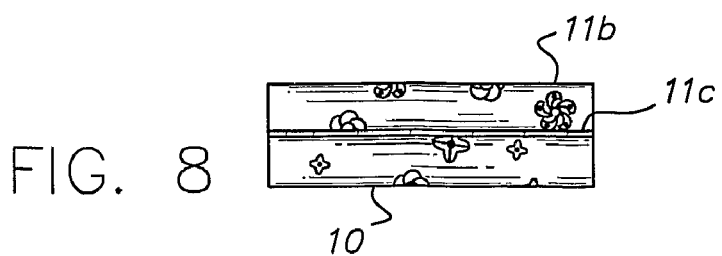
Figure 9:
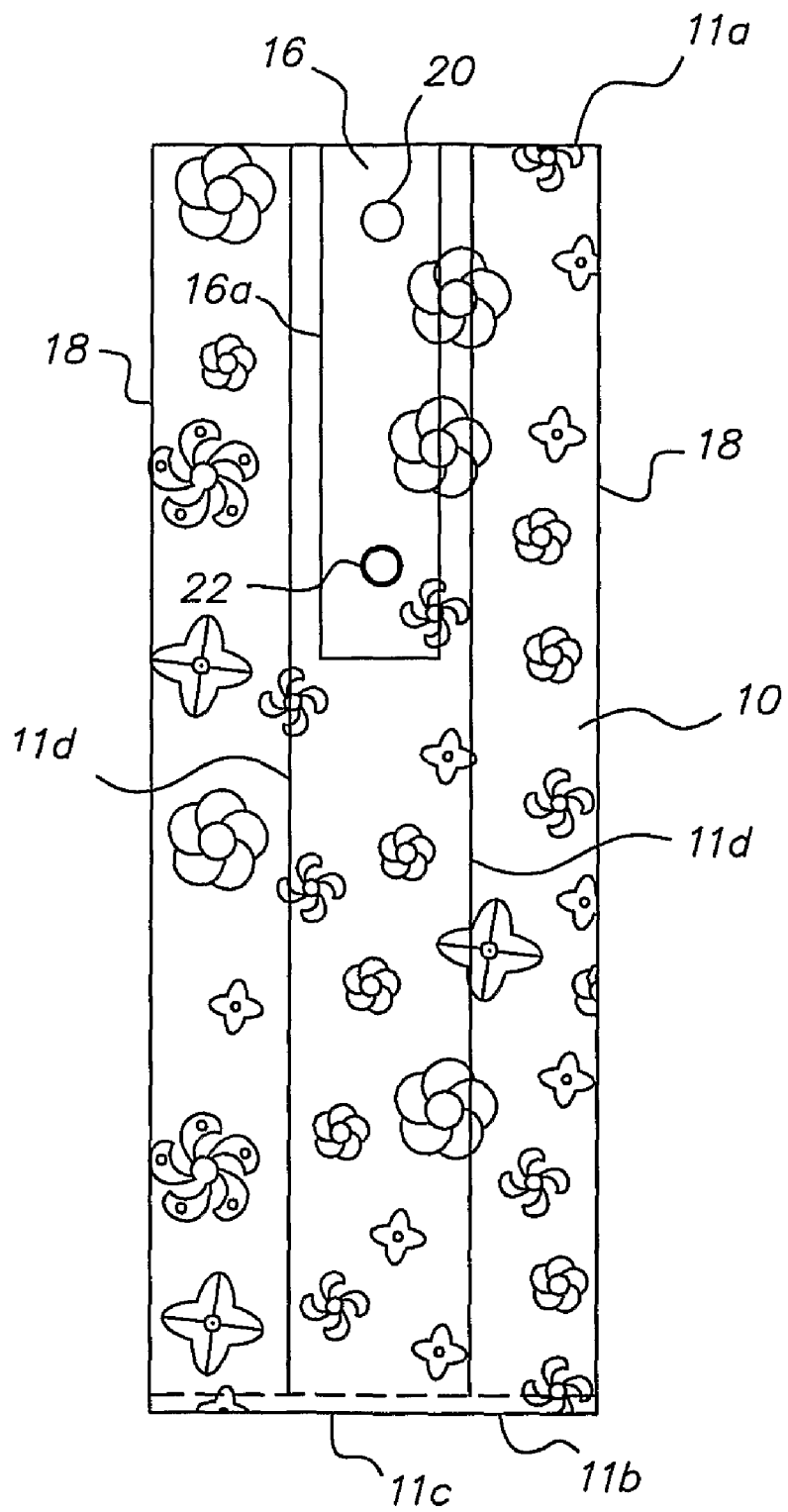
FIG. 9 is a diagram of the bag of FIGS. 1-2 from a front or back view, in which the bag lies flat with gussets folded inward, such as in a condition prior to use of the bag.

Referring to FIGS. 1-9, a bag 10 of thin plastic material is shown having an open end 11a and closed end 11b, and gusseted sides 14 which fold inward between the open and closed ends. The open end 11a has a die cut and perforated portion 16 along edge 16a (see FIG. 9) which when removed by the user or manufacturer form two tying or handle portions 18. Portion 16 is removed prior to use of the bag, and may have a hole 20 for hanging such bag on a hook. For example, hole 20 may be ⅜ inches in diameter, and portion 16 may be about ⅞ inches wide and of a length to provide the desired length of tying portions 18. Multiple bags may be heat-blocked along region 22 (see FIG. 9) of portion 16 so as to couple multiple bags 10 together, such as for storage of said multiple bags for presentation on a hook via hole 20. The closed end 11b is provided by a heat block along edge 11c. For example, bag 10 may be of 0.001" (1 mil) thick material, 3½-3⅜ inches in width, and 9¾-10 inches in length. The two tying portions 18 for example may each be about 4 inches in length and each about 1¾ inches in width from the edge of side 14 to the inner edge 16a parallel to such side edge. The bag 10 may be sized in accordance with the used product to be received in the bag, such that it is limited to receiving but one used product (and other material related to the use or replacement of the product, such as wrappers, inserters, applicators, or the like material). The front 13a and back 13b of the bag may be identical except for a shift in a repeated printed pattern of black, white, or color ink or other imprinting material on their outer surfaces. The gusseted sides 14 fold inward along fold 11d allowing the bag to lie substantially flat, and as best shown in FIGS. 5-7 the gusseted sides expand outward when the bag 10 is in an open position for receiving a feminine hygiene product via open end 11a, or other product needing hygienic disposal, such as a used adult incontinence product. The sides 14 may be about 2 inches wide when the bag 10 is open, and when the bag is closed, fold 11d extends inward about 1 inch from its respective gusseted side 14.

Bag 10 is formed of plastic material, such as a base of High Density Polyethylene (HDPE) resin with additional color resin, antimicrobial resin, and fragrance materials. To make the plastic material colored, such as pastel pink color, an HDPE-compatible color resin is used, such as available from A. Schulman, Inc., Akron Ohio, USA. In the case of a pastel pink color for example, the color resin is of a HDPE specified color matched to Pantone Matching System (PMS) #196.

The antimicrobial resin may be, for example, Polybatch ASX 502 resin, also available from A. Schulman, Inc. Preferably, the antimicrobial resin provides an antimicrobial agent in the plastic material which is EPA registered as being effective against a wide spectrum of microorganisms, such as e-coli bacteria and fungus. Preferably, the color and antimicrobial resins are compounded together, and such compound color and antimicrobial resin products are also available from A. Schulman, Inc. Resulting compounded color and antimicrobial resins may be of 6% Amorphous Silica and 60% Titanium Dioxide.

The fragrance is a poly based material or Perfumery Compound, such as available from International Flavors and Fragrances (IFF), of Hazlet, N.J., USA. For example, the fragrance may be IFF catalog number XBF-800230, Sweet Dreams, and such material may be a Poly IFF Concentrate when supplied in pellet form. As other base plastic resins, color resin, and antimicrobial resin components may be used, such components are not limited to those specified herein. For example, the bag's plastic material may be of a base material of combined HDPE and Low Density Polyethylene (LDPE) resins with color compatible resin, antimicrobial resin, and fragrance materials.

Pellets providing the compounded color and antimicrobial resins, fragrance, and base resin(s) are mixed together in a hopper, heated to a point where the material is extruded into a thin film, formed into a tube of specified thickness, width and gusset, imprinted, and die cut into its final shape. When so mixed together, the fragrance material is combined in 2% ratio with base resin(s). The compounded color and antimicrobial resins are combined with the base resin(s) in the hopper to obtain the desired color and antimicrobial strength. The compounded color and antimicrobial resins may for example be in a 5% ratio (e.g., Let Down Ratio) when combined with base resin materials. Other methods for combining the components of the bag plastic material may also be used.

Figure 10C:
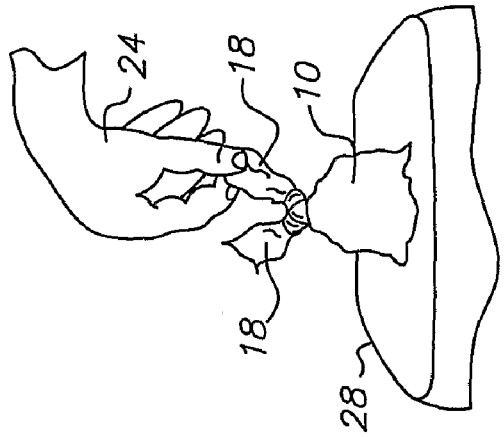
FIGS. 10A-10C illustrate the steps for using of the bag of the present invention.
Figure 10B:
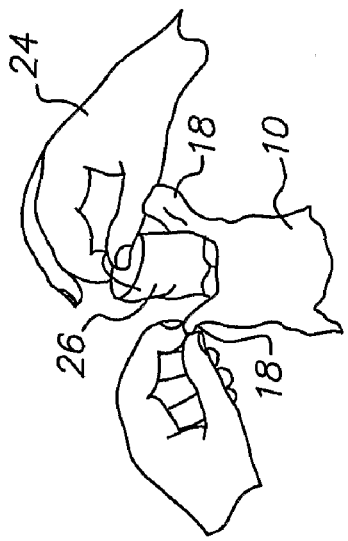
Figure 10A:
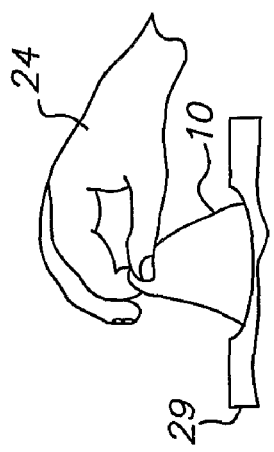

As shown in FIGS. 10A-C, bag 10 is a one-time use bag which a user 24 (illustrated by a hand) can place a used feminine hygiene product 26 (e.g., pads, tampons, sanitary napkins, and panty liners and any wrappers, plastic or cardboard inserters or applicators, associated with the used product or the user's replacement product), or other used individual product where hygienic disposal is desired (e.g., used adult incontinence underwear or pad), ties or knots tying portions 18, and drops into waste receptacle 28 in bathroom or restroom. The knotted tying portions 18 effectively seal in contents 26 reducing risk of contact with germ-laden items.

The bag's embedded floral fragrance provides pleasant fresh scent, masking odors, for overall appeal to users. The bag's built in antimicrobial agent inhibits the growth of odor causing bacteria. The color (preferably pastel pink) and imprinted design (preferably of darker reddish pink color and of a floral pattern but other pattern may be used with or without other markings, or text related to bag use) assists in concealment or obfuscation of the bag's content to the human eye. In other words, since the bag's thin material, which enables the bag to be easily handled, tied, and packaged in a dispenser, allows transmission of light there through the pink color, both the selected color (i.e., of the bag and imprint) and the imprinted design hinders the ability of the human eye to perceive the contents of the bag which may have pink or reddish blood stains. Use of the bag provides an alternative to flushing in toilet and thereby serves to significantly reduce costly clogs in toilets and plumbing systems from paper and heavy absorbent fiber based items used in feminine hygiene products. The used feminine product need not be wrapped in toilet paper or any wrapper or material prior to being located in bag 10, as the bag efficiently seals the used product, eliminating risk of leakage when sealed properly by tying or knotting portions 18. Furthermore, since the used product is sealed in bag 10 it may be placed in a container specifically designated in public bathrooms, or disposed of within a general waste product basket, bin, or receptacle, without risking contact by user or cleaning personnel to the contents potential infectious diseases. Such specifically designated or general receptacle is of a size capable of receiving multiple tied bags 10 each with used material.

Figure 11A:
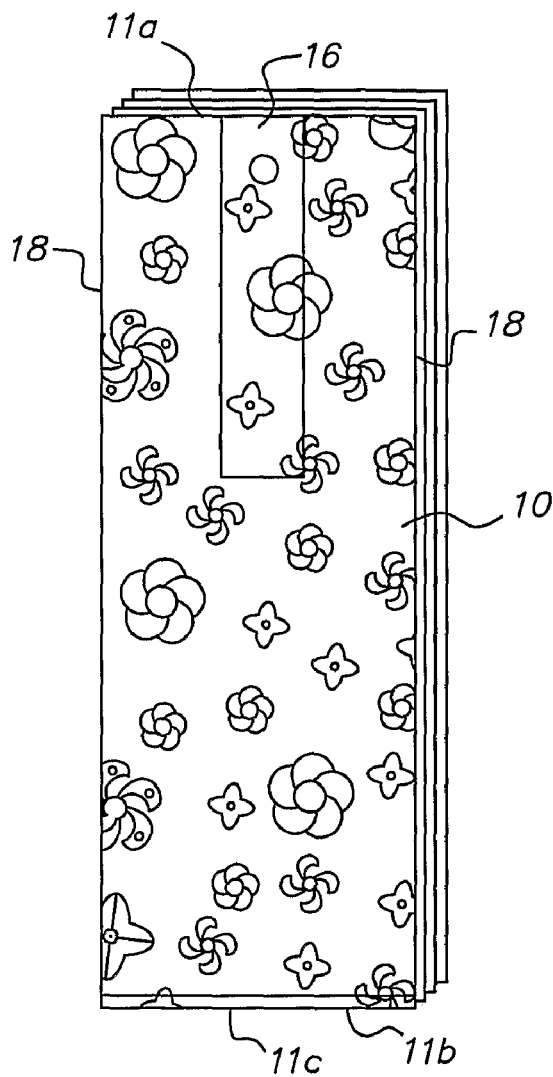
FIG. 11A shows an example of a stack of multiple bags of FIGS. 1 and 2.
Figure 11B:
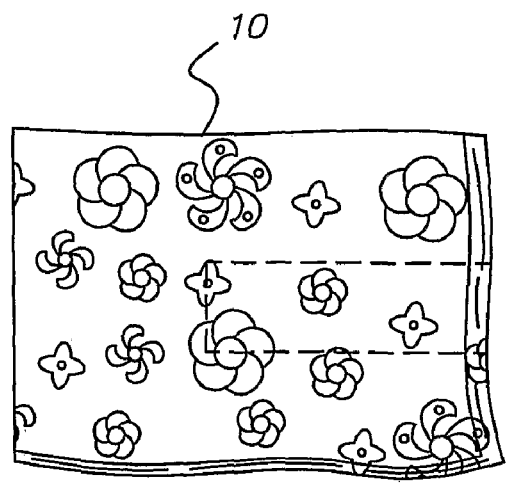
FIG. 11B shows an example of a stack of FIG. 11A in which the bags are folded over.

FIGS. 11A and 11B shows a stack of multiple bags 10 in a flat and folded over configuration, respectively. When stacked together and folded over, they may be assembled in a dispenser, such as the portable dispenser shown for example in FIGS. 12A and 12B. In this example, the folded stack is located on a base 30 of dispenser 29, a bottom 31 is folded over the stack and base 30, and then flaps 32 folded form a pocket with the bottom 31. Edge 31a may be attached, such as by adhesive to base 30 when folded over the base. Flaps 32 may be attached to bottom 31 by adhesive. An opening (or removable perforated portion) 33 enables the user to pull out individual bags from the dispenser 29. Alternatively, the bags 10 may each be folded over and interweaved with each other such that dispensing of one bag exposes (or pops up) either end 11a or 11b of the bag underneath from the dispenser opening. A cover 34 may fold over the pocket formed by bottom 31 and flaps 32, having a tongue 34a which may received in a slit 35 in bottom 31, as shown in FIG. 12A. Opening 33 is shown as a dashed line to indicate that that it lies under cover 34 in FIG. 12A. Dispenser 29 enables multiple bags to be easily carried by a user (e.g., up to 20-30 bags), such as in a purse, handbag, backpack, or pocket. Such enables the bags to be present when the user needs them. The dispenser 29 may be made of cardboard or polyethylene, and is disposable when all bags are used. Portions 16 of the bags may be removed prior to locating the stack of bags in dispenser 29, or removed by the user prior to use of the bag.

Figure 12B:
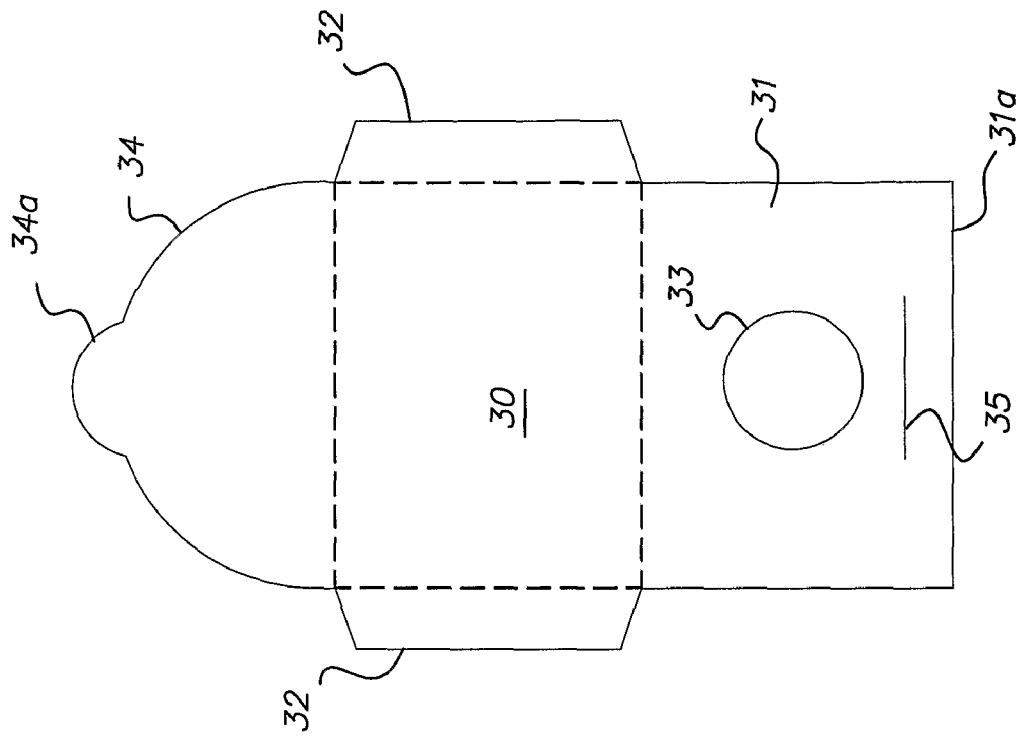
FIG. 12B is a cutout form for assembly of the dispenser of FIG. 12A.
Figure 12A:
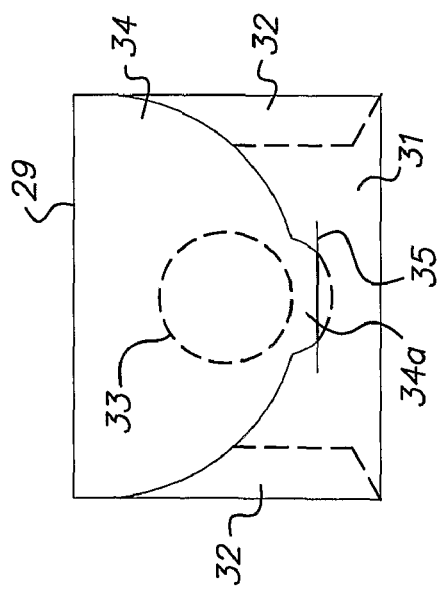
FIG. 12A is a portable dispenser for use in storing multiple bags of FIGS. 1 and 2 which enable single bag dispensing therefrom.

Other dispensers may be used than shown in FIGS. 12A-B. As such, multiple bags 10 may be placed in any container in fold-over, flat, or interweave fold-over fashion, which has an opening to individually dispense the bags. Such container may be portable or fixed, such as mounted to the wall or stall of a bathroom or restroom. In the case of a portable dispenser, the opening may be a slit or a fold-over slit, such as typically used in plastic portable tissue packages. Thus, the bag is of a thin material and may be made sufficiently small in size to enable multiple bags to be compact when oriented substantially flat and adjacent to each other in a fixed or portable dispenser in one of at least a stack, folded, or interweave condition.

From the foregoing description, it will be apparent that an improved disposable bag for hygienic disposal of a used product has been provided. Variations and modifications of the herein described bag, dispenser, and method of use, other applications for the invention will undoubtedly suggest themselves to those skilled in the art. Accordingly, the foregoing description should be taken as illustrative and not in a limiting sense.

The invention claimed is:

1. A bag for hygienic disposal of a used product comprising:
    thin plastic material shaped into a container having a closed end and an open end cut to provide two tying portions, and sides extending between the open and closed ends;
    said plastic material having at least an antimicrobial agent in the plastic material when said plastic material is formed, in which said bag enables receiving only one used product along with any non-human bodily material associated with use or replacement of said product by a user of said used product, and said tying portions represent two handles tieable to retain said product within said bag; and
    imprinted material along said plastic material, wherein said plastic material allows transmission of light there through, and said imprinted material and said plastic material are each of a different type of a color red to enable said imprinted material and said plastic material to operate together to hinder perception of human bodily material associated with use by the user of said used product when said human bodily material is received in said bag with said used product and said human bodily material comprises blood.

2. The bag according to claim 1 wherein said product is a used feminine hygiene product.

3. The bag according to claim 1 wherein said product is a used incontinence product.

4. The bag according to claim 1 wherein said sides have gussets which fold said sides inward toward each other.

5. The bag according to claim 1 wherein said imprinted material forms a pattern on said plastic material.

6. The bag according to claim 1 wherein said size of said bag is in accordance with the size of the used product to be received in said bag.

7. The bag according to claim 1 wherein a plurality of ones of said bag are provided in a dispenser for individually dispensing each of said plurality of ones of said bag.

8. The bag according to claim 7 wherein each of said plurality of ones of said bag is sufficiently small in size to enable said plurality of ones of said bag to be compact when in said dispenser.

9. The bag according to claim 7 wherein said dispenser is mountable to the wall or stall of a bathroom or restroom.

10. The bag according to claim 7 wherein said dispenser is portable.

11. The bag according to claim 1 wherein said bag is sufficiently small in size to enable a plurality of ones of said bag to be compact when oriented substantially flat in a fixed or portable dispenser in one of at least a stack, folded, or interweave condition.

12. The bag according to claim 1 further comprising a fragrance resin mixed into said plastic material when said plastic material was formed.

13. The bag according to claim 1 wherein said tying portions are present and tieable prior to said bag being provided to the user.

14. The bag according to claim 1 wherein said imprinted material is of the color red darker than the color red of said plastic material to further enable said imprinted material and said plastic material to operate together to hinder perception of any blood when received within the bag with the used product.

15. The bag according to claim 14 wherein said type of red color of said plastic material is pink.

16. The bag according to claim 1 wherein said imprinted material is at least a repeating pattern along said outer surface.

17. The bag according to claim 1 wherein no unused hygiene or incontinence product is at any time externally attached to said bag prior to use.

18. The bag according to claim 1 wherein said bag when folded is only folded over said bag or another one of said bag.

19. The bag according to claim 1 wherein said tying portions are an integral part of the bag when knotted, said tying portions are tieable prior to said bag being provided to the user, and no unused product is at any time externally attached to said bag.

20. A method for hygienic disposal of a used product comprising the steps of:
    forming thin plastic material having at least an antimicrobial agent;
    providing a bag of said plastic material having imprinted material along an outer surface of the bag in which said imprinted material and said plastic material are each of a different type of a color red to enable said imprinted material and said plastic material to operate together to hinder perception of any blood upon said used product when in said bag;
    inserting in said bag a used product along with any non-human bodily material associated with use or replacement of said product by a user of said product; and
    tying two portions extending from said bag after said inserting step is carried out to retain said product within said bag.

21. The method according to claim 20 further comprising the step of disposing said tied bag in a receptacle capable of receiving a plurality of ones of said bag with a used product.

22. The method according to claim 20 wherein said product is a used feminine hygiene product.

23. The method according to claim 20 wherein said product is a used incontinence product.

24. The method according to claim 20 wherein said forming step further comprises the step of forming said thin plastic material having at least an antimicrobial agent and fragrance.

25. A bag for hygienic disposal of a used feminine hygiene product in a general waste product basket, bin, or receptacle without risk of contact by other persons to any contents of said bag having a potential infectious disease, said bag comprising:

a thin film of plastic material shaped into a container having a closed end and an open end cut to provide two tying portions enabling knotting with each other to close the open end, and inward foldable gusseted sides extending between the open and closed ends;

said plastic material comprises at least an antimicrobial resin and a fragrance resin mixed in the plastic material when said plastic material is formed, in which said bag enables receiving only one used feminine hygiene product along with any material associated with use or replacement of said feminine hygiene product by a user of said feminine hygiene product;

imprinted material of a repeating pattern along the outside of said container, wherein said plastic material allows transmission of light there through, and said imprinted material and said plastic material are each of a different shade of pink to configure said imprinted material and said plastic material to operate together to hinder perception of human bodily material upon a used feminine hygiene product when a used feminine hygiene product is received in said bag;

said tying portions are tieable in a knot to retain said used feminine hygiene product when present in said bag so that said bag with the used feminine hygiene product is locatable within a general waste product basket, bin, or receptacle without risk of contact by other persons to any contents of said bag having a potential infectious disease;

said tying portions are an integral part of the bag when knotted, and said tying portions are tieable prior to said bag being provided to the user, wherein no unused feminine hygiene product is at any time externally attached to said bag;

said antimicrobial resin of the plastic material being sufficient to inhibit growth of odor causing bacteria upon a used feminine hygiene product when present in said bag;

said fragrance agent of the plastic material being sufficient to provide scent to mask any odors from a used feminine hygiene product when present in said bag; and said bag is sufficiently small in size to enable a plurality of ones of said bag to be compact when oriented substantially flat in a fixed or portable dispenser in one of at least a stack, folded, or interweave condition.

26. The bag according to claim 25 wherein said size of said bag is in accordance with the size of a used feminine hygiene product to be received in said bag.

27. The bag according to claim 25 wherein said dispenser is a portable dispenser having an opening, and a plurality of ones of said bag are provided in said dispenser for individually dispensing each of said plurality of ones of said bag via said opening.

28. The bag according to claim 25 wherein said dispenser is a fixed dispenser mountable to the wall or stall of a bathroom or restroom.

29. The bag according to claim 25 wherein said dispenser is portable.

* * * * *